United States Patent [19]

Smith

[11] 4,244,379

[45] Jan. 13, 1981

[54] CHECK VALVE FOR BLOOD DRAWING APPARATUS

[75] Inventor: Gordon E. Smith, Sun Prairie, Wis.

[73] Assignee: Quest Medical, Inc., Carrollton, Tex.

[21] Appl. No.: 63,033

[22] Filed: Aug. 2, 1979

[51] Int. Cl.³ .............................................. A61B 5/14
[52] U.S. Cl. ............................ 128/766; 128/218 NV
[58] Field of Search ................... 128/215, 216, 218 R, 128/766, 218 NV

[56] References Cited

U.S. PATENT DOCUMENTS

| | | | |
|---|---|---|---|
| 3,577,980 | 5/1971 | Cohen | 128/766 |
| 3,817,240 | 6/1974 | Ayres | 128/766 |
| 3,848,579 | 11/1974 | Villa-Real | 128/766 |

Primary Examiner—John D. Yasko
Attorney, Agent, or Firm—Isaksen, Lathrop, Esch, Hart & Clark

[57] ABSTRACT

A check valve is disclosed for use in blood drawing apparatus wherein it is desired to draw multiple samples from a single needle inserted into a patient's arm for use in a variety of medical tests. The check valve includes therein a valve member formed of a piece of a silicone elastomer which has a slit formed therein, the slit opening only when fluid pressure is greater in the patient than in the vessel into which the blood is being drawn. The check valve is of particularly small size so that it may be mounted within a conventionally sized double-needle fitting normally used in blood drawing apparatus.

5 Claims, 4 Drawing Figures

CHECK VALVE FOR BLOOD DRAWING APPARATUS

BACKGROUND OF THE INVENTION

1. Field of the Invention

The present invention relates to apparatus for drawing blood from patients, and, in particular, to a check valve to be mounted within a fitting designed to be inserted into a patient to allow multiple blood samples to be drawn from the patient.

2. Description of the Prior Art

In drawing multiple blood samples from a patient for use in a variety of diagnostic medical tests, it is conventionally the practice to insert one needle fitting into the patient which is used to sequentially fill a series of containers for a variety of these tests. Usually a fitting having a needle mounted on both ends thereof has one needle inserted into the patient. Then a series of evacuated fluid containers used for the various blood tests, or alternatively syringes with a puncturable end seal, are inserted onto the opposite needle so that blood may be drawn through the fitting. When this is done however, usually blood drips from the patient from the open end of this double ended fitting between the drawing blood for the various samples. Also, when a syringe is used, it occasionally happens that a technician or aide who is drawing blood through the fitting with a syringe may inadvertently press down on the syringe re-injecting blood back from the syringe into the patient. Since it is often the practice when conducting various blood tests to include a reagent in the vessel being filled directly from the patient, it is occasionally the case that when such re-injection is made, unwanted or undesirable reagents may be inadvertently injected into the patient. Some prior art fitting included one movable needle which punctured a membrane to allow fluid flow only when a receptacle was attached to the fitting, but no prior art check valve is known suitable for use in such blood drawing apparatus.

SUMMARY OF THE INVENTION

The present invention is summarized in that a check valve for blood drawing apparatus includes a body member having a cavity formed therein opening to the exterior of the body member at one end thereof, a proximal needle extending into the cavity in the body member, a plug received in the opening of the cavity in the body member to close the cavity, a distal needle also extending through the plug into the cavity in the body member, and a flexible valve member positioned in the cavity in the body member blocking the path of the fluid flow from the proximal needle to the distal needle, the valve member having a slit formed therein so that the slit will be caused to open to allow fluid flow therethrough when the fluid pressure in the proximal needle is greater than the fluid pressure in the distal needle the valve member being held in place by the plug.

It is an object of the present invention to provide a check valve for blood drawing apparatus that is suitable for use in a blood-sampling fitting of conventional size and shape.

It is another object of the present invention to provide such a check valve that is extremely efficient in preventing re-injection of blood or other material back into a patient.

It is yet another object of the present invention to provide such a check valve which is entirely formed of a biologically inert material.

Yet other objects, advantages, and features of the present invention will become apparent from the following specification when taken in conjunction with the accompanying drawings.

DESCRIPTION OF THE PREFERRED EMBODIMENT

Figure 1:
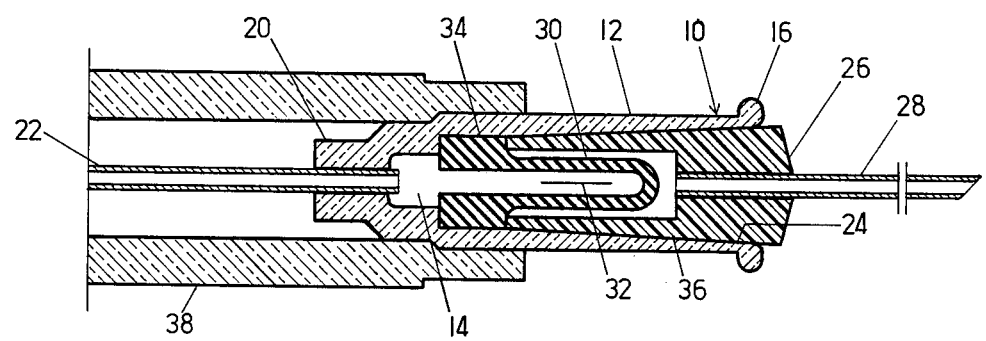
FIG. 1 is a longitudinal cross-section view of a check valve for blood drawing apparatus constructed in accordance with the present invention.

Shown in FIG. 1 is a check valve for blood drawing apparatus, indicated generally at 10, constructed in accordance with the present invention. The check valve 10 includes a main body member 12 which is formed as a single molded piece of glass, plastic, or other biologically inert rigid material preferably of a transparent or translucent character. The body member 12, which is generally elongated in its shape, has a longitudinally extending cavity 14 formed within it with the cavity 14 having an opening formed opening to the exterior of the body member 12 at the distal end of the body member 12, with the distal end of the body member 12 around the opening being indicated at 16. The distal end 16 of the body member 12 and a proximal end 20 of the body member 12 may be provided with ribs or other projections so as to be easily grasped by hand. Extending from and through the proximal end 20 of the body member 12 is a proximal needle 22. This proximal needle 22 extends through the proximal end 20 of the body member 12 and into the cavity 14 therein, and the body member 12 is molded securely about and is hermetically sealed to the proximal needle 22. The end of the proximal needle 22 received within the cavity 14 in the body member 12 has a flattened end whereas the end of the proximal needle 22 farthest from the body member 12 has a sharpened end (not shown) so as to be readily insertable through the human skin. The proximal needle 22 is formed of metal or other extremely rigid material and is, of course, hollow throughout its length. At its distal end 16 the cavity 14 in the body member 12 is provided with a tapering surface 24 toward the opening at the distal end 16. The tapering surface 24 is formed as a portion of the wall of the cavity 14 tapering outward in the direction of the opening at the distal end 16 of the body member 12. Fitting within the opening in the distal end 16 of the body member 12 is a molded plug 26 which has a taper on its outer surface matching the taper of the tapering surface 24 of the body member 12. The molded plug 26 is formed of glass, hard plastic, or other relatively rigid, biologically inert material. A cylindrical, hollow retaining portion 36 is formed extending in a proximal direction from the plug 26 with the retaining portion 36 sized so as to fit inside of the cavity 14. The molded plug 26 is formed around a distal needle 28 which extends through the molded plug 26 to open into the interior of the cavity 14 inside the body member 12. The distal needle 28 resembles the proximal needle 22 in that it is, of course, hollow throughout its length, and has a flattened interior end opening within the cavity 14 and a sharpened end farthest from the body member 12, though the distal needle need not always be sharpened at its farthest distal end.

Formed at the proximal end of the cavity 14 in the body member 12 is a shelf-like portion which receives pressed thereagainst the skirt portion 34 of a valve member 30. The valve member 30 is preferably composed of a silicone elastomer, but may also be formed of other relatively flexible and biologically inert material. The valve member 30 is formed as a closed, elongated, sleeve-shaped member closed at its end opposite from the proximal needle 22. The valve member 30 is held in place by reason of the skirt portion 34 which is pinched between the retaining portion 36 of the plug 26 and the shelf in the interior of the cavity 14. The valve member 30 is provided with a slit 32 therethrough with the slit 32 being generally aligned with the longitudinal length of the valve member 30, which is similarly aligned with the longitudinal axis of the proximal needle 22. The valve member 30 is formed with a thickness sized so as to selectively determine the force necessary to force open the slit 32 with fluid pressure, as will be explained in greater detail below. A protective sheath 38, of transparent material and corresponding in interior shape to the exterior of the check valve 10 may optionally be positioned over the proximal needle 22 to prevent accidental skin punctures during handling and to keep the needle sterilized and a similar sheath may be provided for the distal needle if desired.

In its operation, the check valve 10 of FIG. 1 operates as a one-way valve to permit blood drawing apparatus to draw blood from a patient, while completely avoiding the possibility of inadvertantly injecting any blood, blood solutions, or foreign material such as reagents or stabilizers back into the patient. The check valve 10 also prevents the unwanted dripping of blood from a patient should the check valve 10 need to be left in a patient for any extended period of time. In using the check valve 10, the proximal needle 22 is used for insertion into the patient. The sharp proximal end of the proximal needle 22, which is the end opposite from the body member 12, is inserted through the skin of the patient and into a vein of the patient. The check valve 10 is then left with the proximal needle 22 inserted into the vein during the entire blood drawing operation even if a larger number of different samples are needed. In order to draw blood through the check valve 10, blood drawing or sampling equipment, such as is conventional in the prior art, is attached to the distal needle 28. The attachment of the blood drawing equipment to the distal needle 28 may be through the means of an evacuated container covered with a membrane into which the distal needle 28 is inserted, or it may be in the form of any other drawing equipment which may secure itself around the distal needle 28. When used with some such equipment, there will be no need for the distal end of the distal needle 28 to be sharpened, and it may have a blunt end. To cause blood to be extracted from the patient, the blood drawing equipment must be able to cause a slight vacuum or suction to be applied through the interior of the distal needle 28 to the cavity 14 within the body member 12. Inasmuch as the blood within the patient is always under pressure, there is a continual positive blood pressure applied to the fluid which occupies the interior of the proximal needle 22 and the interior of the valve member 30. When the slight vacuum or suction is applied to the cavity 14 the pressure of the blood on the interior of the valve member 30 causes the slit 32 in the valve member 30 to open slightly allowing blood to proceed from the proximal needle through the slit 32 of the valve member 30 and into the cavity 14. The blood may then be drawn through the distal needle 28 into the blood drawing or sampling apparatus. Whenever the vacuum is removed from the distal needle 28, i.e. when the needed blood has been drawn, the slit 32 in the valve member 30 closes and no more blood flows through the check valve 10.

The check valve 10, besides ensuring that blood flows from the patient only when desired, also ensures that no treated blood, or other solution or foreign material may be reinjected into the patient. Should a positive pressure greater than the blood pressure be applied through the distal needle 28 to the cavity 14 in the body member 12, the slit 32 will not open. This result occurs because of the flexible nature of the silicone and the circular shape of a cross-section of the valve member 30 which allows a moderate force to force the slit 32 open when the force is applied from the interior, but does not allow the slit 32 to open when the force is applied from the exterior. In fact, if the thickness of the valve member 30 is selected appropriately, the valve member 30 will itself collapse on itself and seal the slit 32 completely to prevent fluid flow in the wrong direction if a great reverse pressure is imposed. Thus, there is no way in which blood solutions or other undesired material can be forced from the cavity 14 through the proximal needle 22 back into the patient.

The molded plug 26 is provided so as to close securely the opening at the distal end 16 of the body member 12 and to secure the valve member 30 mounted therein. The interior of the cavity 14 has formed therein the tapering surface 24 and the exterior of the plug 26 is similarly tapered to allow the plug 26 to be jammed in the body member 12 to form a secure and fluid-tight seal therewith. This construction insures that the check valve 10 is both simple and inexpensive to assemble yet also efficient and secure in its operation.

The structure of the check valve 10 allows it to be quickly and economically manufactured too. First the body member 12 is molded about the proximal needle 22 with the shelf being formed in the cavity after which the valve member 30 is dropped into place. The molded plug 26, with the distal needle 28 molded therein, is then inserted into the open end of the cavity 14 with the retaining portion 36 forcing the skirt portion 34 of the valve member 30 into the distal end of the cavity 14. The tapering surface 24 of the cavity 14 and the taper provided along the exterior of the molded plug 26 allow the molded plug to be jammed securely into the body member 12, with the retaining portion 36 thereby securely jamming the skirt portion 34 and thereby the valve member 30 in fixed position. No further alignment or adjustment of the valve member 30 then need be made with the valve member being thus flawlessly and effortlessly secured in place. Thus the assembly of the check valve 10 is largely accomplished in one easy and simple operation thus requiring a minimum of worker time and care.

Figure 2:
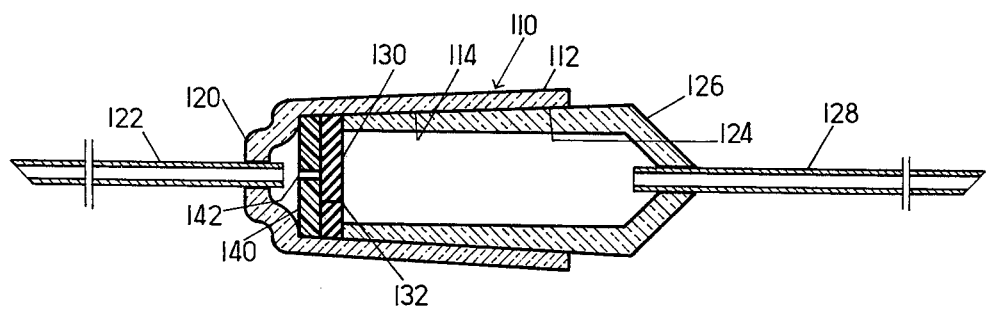
FIG. 2 is an alternative embodiment of a check valve for blood drawing apparatus constructed in accordance with the present invention, also shown in longitudinal cross-sectional view.

Shown in FIG. 2 is another alternative embodiment of a check valve construction in accordance with the present invention. In describing the check valve of FIG. 2, which is indicated generally at 110, the elements of that check valve have been numbered similar to the elements of the check valve 10 of FIG. 1, and only the differences between the check valve 110 of FIG. 2 and the check valve of FIG. 1 will be described in great detail.

Figure 3:
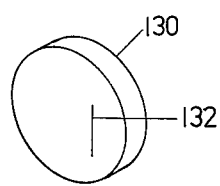
FIG. 3 is a perspective view of the valve member of the check valve of FIG. 2.

In the check valve 110 of FIG. 2, the cavity 114 therein is formed generally as a frusto-conical shape tapering outward toward the proximal end thereof. A small bulbous extension of the cavity 114 is formed to receive therein the distal end of the proximal needle 122. The molded plug 126 is formed as a generally cup-shaped member, with the exterior of the plug 126 having a tapered outer surface corresponding to the tapering interior surface 124 of the cavity 114. The molded plug 126 is generally hollow throughout its length, with the distal needle 128 extending into the base of the cup formed by the molded plug 126. The valve member 130 of the check valve of 110 of FIG. 2 is formed as a flat circular disk of silicone elastomer, or other similar highly flexible material. The valve member 130 is provided with a slit 132 extending therethrough which is positioned eccentrically with regard to the center of the disk valve member 130, as is shown in FIG. 3. Positioned directly behind the valve member 130 is a backing disk 140 formed of rigid plastic or other rigid biologically inert material. The backing disk 140 is provided with a hole 142 extending therethrough, with the hole 142 being formed at the center of the backing disk 140. As can be seen from FIG. 2, the backing disk 140 is positioned directly behind and in contact with the valve member 130, and that these two members together are pressed against the proximal end of the cavity 114 by the molded plug 126.

In its operation, the check valve 110 of FIG. 2 also functions as a one-way valve permitting blood flow from the proximal needle 122 to the distal needle 128 in one direction only, and to prevent inadvertent blood flow when removal of the blood is not desired. The valve member 130 of the check valve 110 of FIG. 2 is normally in an unflexed position as shown in FIG. 2. When however, a suction or slight vacuum is applied to the interior of the cavity 114 through the interior of the plug 126 through the distal needle 128, the valve member 130 flexes outward, and the slit 132 is forced open. When this occurs, blood may travel from the proximal needle 122 through the hole 142 in the backing disk 140 and then through the slit 132 in the valve member 130. When however, the pressure is in the incorrect direction, i.e. greater in the distal needle 128 than in the proximal needle 122, the valve member 130 is merely forced against the backing disk 140, and the slit 132 does not open thereby preventing any fluid flow in the incorrect direction. The thickness of the valve member 130 is selected so as to ensure that a predetermined positive pressure is necessary to open the valve member 130, so that the normal blood pressure of the patient alone will not open the valve member 130.

Figure 4:
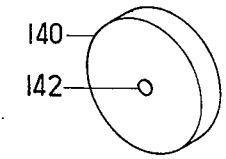
FIG. 4 is a perspective view of the backing disk of the check valve of FIG. 2.

The check valve 110 of FIGS. 2-4 is constructed by first molding the body member 112 about the proximal needle 122. Then the backing disk 140 and the valve member 130 are inserted into the open end of the cavity 114 in that order. Then the molded plug 126 with the distal needle 128 may be inserted into the cavity 114 and jammed securely therein. The open front end of the cup-shaped molded plug 126 contacts the valve member 130 and jams the valve member 130 and the backing disk 140 securely against the distal end of the interior of the cavity 114.

The provision for the centrally located hole 142 in the backing disk 140 and the eccentric slit 132 in the valve member 130 is a particular advantage in assemblying the check valve 110 inasmuch as no mutual alignment between these two parts is required. Thus, if the hole 142 were also eccentrically located, it would be necessary for the person assemblying the check valve 110 to position the two so that the slit 130 did not end up positioned over the hole 142 in order to ensure proper one-way operation of the device. But with the hole 142 centrally located and the slit 132 eccentrically located, no such careful positioning is required, inasmuch as the slit 130 will not be positioned over the hole 142 no matter what the relative rotational position of the two components.

It is understood that the present invention is not limited to the particular construction and arrangement of parts disclosed and illustrated herein, but embraces all such modified forms thereof as come with the scope of the following claims.

I claim:

1. A check valve for blood drawing apparatus comprising:
    a body member having a cavity formed therein opening to the exterior of the body member at one end thereof;
    a proximal needle extending into the cavity in the body member;
    a plug received, in the opening of the cavity in the body member to close the cavity;
    a distal needle also extending through the plug into the cavity in the body member;
    a flexible valve member in the shape of a flat circular disk positioned in the cavity in the body member to the distal needle, the valve member having a slit formed therein so that the slit will be caused to open to allow fluid flow therethrough when the fluid pressure in the proximal needle is greater than the fluid pressure in the distal needle, the valve member being held in place by the plug; and
    a backing disk formed of rigid material and having a hole formed therein, the backing disk being positioned against and behind the valve member.

2. A check valve as claimed in claim 1 wherein the slit is positioned eccentrically in the valve member and the hole is positioned centrally in the backing disk so that the valve member and the backing disk may be positioned in any rotational orientation relative to each other.

3. A check valve as claimed in claim 2 wherein the cavity in the body member is of a frustro-conical shape with the opening being the larger end thereof and wherein the plug member is a cup-shaped member the exterior of which is sized and shaped to correspond to the interior shape of the cavity so as to be received therein so as to pin the valve member against the backing disk in the interior of the cavity.

4. A check valve for blood drawing apparatus comprising:
    a body member having a cavity formed therein;
    a proximal needle extending into the cavity in the body member;
    a distal needle also extending into the cavity in the body member;
    a backing disk located in the cavity in the body member positioned in the path of fluid flow therethrough, the backing disk having a hole formed therein; and a flexible valve member formed in the shape of a circular disc located against the backing disk such that the backing disk is interposed between the valve member and the proximal needle, the valve member having a slit formed therein to allow fluid flow through the hole in the backing disk and then through the slit in the valve member when the fluid pressure is greater in the proximal needle and to allow the slit to close against the backing disk to prevent fluid flow therethrough when the fluid pressure is greater in the distal needle.

5. A check valve as claimed in claim 4 wherein the hole is centrally positioned in the backing disk and the slit is eccentrically positioned in the valve member so that the backing disk and the valve member may be positioned in any rotational relation relative to each other.

* * * * *